United States Patent [19]

Ost et al.

[11] 4,102,910

[45] Jul. 25, 1978

[54] DERIVATIVES OF CYCLOPROPANE

[75] Inventors: Walter Ost, Bingen; Klaus Thomas, Gau-Algesheim; Ricarda Prokic-Immel, Mainz, all of Fed. Rep. of Germany

[73] Assignee: Celamerck GmbH & Co. KG., Ingelheim am Rhein, Fed. Rep. of Germany

[21] Appl. No.: 808,435

[22] Filed: Jun. 20, 1977

[30] Foreign Application Priority Data

Jun. 22, 1976 [DE] Fed. Rep. of Germany ....... 2627779

[51] Int. Cl.² ................... C07C 119/18; C07C 123/00
[52] U.S. Cl. ........................ 260/453 RW; 260/564 R; 424/298; 424/326
[58] Field of Search ................... 260/453 RW, 564 R

[56] References Cited

U.S. PATENT DOCUMENTS 3,972,931  8/1976  McCarthy, Jr. ................. 260/564 R Primary Examiner—Lewis Gotts
Assistant Examiner—Robert C. Whittenbaugh
Attorney, Agent, or Firm—Hammond & Littell

[57] ABSTRACT

Compounds of the formula

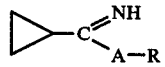

wherein
  A is oxygen or —NH—, and
  R is straight or branched alkyl of 2 to 22 carbon atoms or straight or branched alkenyl of 3 to 18 carbon atoms, and acid addition salts thereof; the compounds as well as the salts are useful as acaricides.

4 Claims, No Drawings

DERIVATIVES OF CYCLOPROPANE

This invention relates to novel cyclopropane derivatives, as well as to acaricidal compositions containing certain cyclopropane derivatives as active ingredients.

More particularly, the present invention relates to acaricidal compositions containing as an active ingredient a compound of the formula

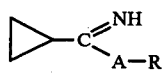 (I)

wherein

A is oxygen or —NH—, and

R is straight or branched alkyl of 2 to 22 carbon atoms, or an acid addition salt thereof.

Formula I embraces known as well as new compounds. The new compounds are those where R is alkenyl of 3 to 18 carbon atoms, or, when A is oxygen, R is alkyl of 3 to 22 carbon atoms, or, when A is —NH—, R is alkyl of 2 to 22 carbon atoms; and acid addition salts thereof.

Those compounds of the formula I wherein A is oxygen may be obtained in the form of their hydrochlorides by reacting cyclopropyl cyanide with an alcohol of the formula

wherein R has the same meanings as in formula I, in the presence of anhydrous hydrogen chloride. The reaction is carried out at a temperature between about −30° and +50° C, preferably between about −10° and +30° C, in a suitable solvent medium. Examples of suitable solvents are diethyl ether, dioxane, chlorinated aliphatic hydrocarbons such as methylene chloride, or aromatic hydrocarbons such as toluene, xylene or benzene. However, a sufficient excess of the alcohol ROH may also serve as the solvent medium.

The hydrochlorides may be converted into other acid addition salts by liberating the free imino ester with an inorganic or organic base and converting the base into the desired acid addition salt with the corresponding acid in conventional manner.

Those compounds of the formula I wherein A is —NH— may be obtained by reacting an imino ester of the formula

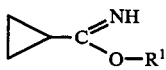 (II)

wherein $R^1$ is an optionally substituted aliphatic radical such as R, as defined above, a cycloaliphatic radical or benzyl, with an amine of the formula

wherein R has the same meanings as in formula I.

The reaction is carried out at a temperature between about −10° and +120° C, preferably between 20° and 80° C, optionally in the presence of a solvent medium which is sufficiently inert under the reaction conditions, such as an alcohol, tetrahydrofuran, dioxane or ethyl acetate. A sufficient excess of the amine $RNH_2$ may also serve as the solvent medium.

Preferred starting compounds of the formula II are those wherein $R^1$ is methyl or ethyl, and they are advantageously used in the form of their salts.

The following examples illustrate the present invention and will enable others skilled in the art to understand it more completely. It should be understood, however, that the invention is not limited solely to the particular examples given below.

EXAMPLE 1

Cyclopropyl-imino-O-ethyl ester hydrochloride

A slow stream of dry gaseous hydrogen chloride was passed for 3 hours through a solution of 3.35 gm (0.05 mol) of cyclopropyl cyanide in 50 ml of ethanol at −2° C. The resulting mixture was allowed to stand for 20 hours at room temperature and was then evaporated in vacuo. The crystalline residue was triturated with ether, suction-filtered and dried, yielding 7.4 gm (100% of theory) of colorless crystals of the compound of the formula

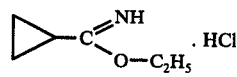

having a decomposition point of 118° C.

EXAMPLE 2

Cyclopropyl-imino-O-n-butyl ester hydrochloride

A slow stream of hydrogen chloride was passed for 3 hours through a solution of 3.4 gm (0.05 mol) of cyclopropyl cyanide and 3.7 gm (0.05 mol) of n-butanol in 60 ml of dry ether. The resulting mixture was allowed to stand for 4 hours at room temperature and was then evaporated in vacuo. The crystalline residue was recrystallized from acetonitrile, yielding 5.4 gm (62% of theory) of colorless crystals having a decomposition point of 118° C, which were identified to be the compound name in the heading.

EXAMPLE 3

Using the procedure described in Example 2, cyclopropyl-imino-O-n-octyl ester hydrochloride, decomposition point 110° C, was prepared from cyclopropyl cyanide and n-octanol.

EXAMPLE 4

Using the procedure described in Example 2, cyclopropyl-imino-O-n-dodecyl ester hydrochloride, decomposition point 113° C, was prepared from cyclopropyl cyanide and n-dodecanol.

EXAMPLE 5

Using the procedure described in Example 2, 100% of theory of cyclopropyl-imino-O-n-hexadecyl ester hydrochloride, decomposition point 108°–110° C, was obtained from cyclopropyl cyanide and n-hexadecanol in toluene or methylene chloride as a solvent.

EXAMPLE 6

Cyclopropyl-N-n-butyl-amidine hydrochloride

A solution of 5.95 gm (0.04 mol) of cyclopropyl-imino-O-ethyl ester hydrochloride (see Example 1) and 3 gm (0.04 mol) of n-butylamine of 50 ml of ethanol was heated at 78° C for 6 hours. Thereafter, the ethanol was distilled off, and the crystalline residue was recrystallized from acetonitrile, yielding 6.7 gm (95% of theory) of the colorless crystalline compound of the formula

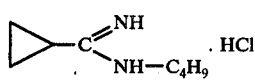

which had a melting point of 138°–141° C.

EXAMPLE 7

Using a procedure analogous to that described in Example 6, except that the liquid distillation residue was extracted with n-hexane and the extract was dried in a fine vacuum, cyclopropyl-N-n-dodecyl-amidine hydrochloride, a colorless oil, was obtained from cyclopropyl-imino-O-ethyl ester hydrochloride and n-dodecylamine.

EXAMPLE 8

Using a procedure analogous to that described in Example 6, except that the raw product was washed with n-hexane and then dried in vacuo, cyclopropyl-N-n-oleyl-amidine hydrochloride, a colorless oil, was obtained from cyclopropyl-imino-O-ethyl ester hydrochloride and oleylamine.

EXAMPLE 9

Cyclopropyl-imino-O-n-hexadecyl ester nitrate (a) 34.5 gm (0.1 mol) of cyclopropyl-imino-O-n-hexadecyl ester hydrochloride (see Example 5) were suspended in a mixture of 100ml ice water and 200 ml diisopropyl ether, and, while cooling and vigorously stirring the suspension, a suspension of 9.4 gm (0.12 mol) of sodium bicarbonate in 30 ml of water was added. The resulting mixture was vigorously stirred for 30 minutes while cooling it on an ice bath, whereby the suspended solids went into solution. The organic phase was then separated, dried over sodium sulfate and evaporated in vacuo at 20° C, yielding 31 gm (100% of theory) of the free imino ester as a wax-like substance having a melting point of 33° C.

(b) 6.2 gm (0.02 mol) of the free imino ester thus obtained were dissolvedin 150 ml of diisopropyl ether, and then 1 ml of aqueous 65% nitric acid was added dropwise, whereupon a precipitate formed. The resulting mixture was stirred at room temperature for 30 minutes, and then the precipitate was collected by suction filtration, washed first with a little ice water and subsequently with acetone, and finally dried. 6.4 gm (87%) of theory) of the colorless crystalline nitrate having a melting point of 83° C were obtained.

EXAMPLE 10

Using a procedure analogous to that described in Example 9(b), cyclopropyl-imino-O-n-hexadecyl ester citrate, a colorless crystalline substance, having a melting point of 95° C, was obtained from cyclopropyl-imino-O-n-hexadecyl ester and citric acid.

EXAMPLE 11

Using a procedure analogous to that described in Example 9(b), cyclopropyl-imino-O-n-hexadecyl ester p-dodecylbenzenesulfonate was obtained from cyclopropyl-imino-O-n-hexadecyl ester and p-dodecylbenzene-sulfonic acid.

EXAMPLE 12

Using a procedure analogous to that described in Example 2, 99% of theory of cyclopropyl-imino-O-n-octadecyl ester hydrochloride was obtained from cyclopropyl cyanide and n-octadecanol in toluene.

EXAMPLE 13

Using a procedure analogous to that described in Example 2, 100% of theory of cyclopropyl-imino-O-eicosanol-(1) ester hydrochloride was obtained from cyclopropyl cyanide and eicosanol-(1) in methylene chloride.

EXAMPLE 14

Using a procedure analogous to that described in Example 2, 98% of theory of cyclopropyl-imino-O-docosanol-(1) ester hydrochloride was obtained from cyclopropyl cyanide and docosanel-(1) in methylene chloride.

The compounds embraced by formula I above and their salts have useful pesticidal properties. More particular, they exhibit acaricidal properties and are particularly effective against aphids, such as Tetranychus urticae, for example. Particularly effective are those compounds of the formula I and their salts where R comprises 12 or more carbon atoms, and the preferred embodiment of A is oxygen.

Examples of suitable acid addition salts are primarily those formed with hydrochloric acid, hydrobromic acid, nitric acid, sulfuric acid, perchloric acid, benzenesulfonic acid, dodecylbenzenesulfonic acid, lactic acid or citric acid.

The capability of the compounds of the formula I and their acid addition salts of reducing the aphid population is due partly to an ovicidal effect and partly to a fertility-inhibiting effect. Because of this mechanism of action, the effect of the compounds of this invention, in contrast to that of commercially available acaricides, is not immediately discernable after their application but only after a few days and often reaches its maximum only after a few weeks.

This delayed action is illustrated by the following table which shows the effect of a few compounds of this invention upon the infestation of bean plants with Tetranychus urticae in terms of percent infestation of untreated controls over a period of 19 days.

| Compound of | % infestation after | | | |
| Ex. No | 6 | 11 | 15 | 19 days |
| --- | --- | --- | --- | --- |
| 1 | 55 | 15 | 9 | 5 |
| 2 | 36 | 29 | 22 | — |
| 9 | 5 | 1 | 1 | — |

Of particular importance is the fact that the compounds of this invention are highly effective against aphids which are resistant against acaricides of the phosphoric acid ester type.

For the purpose of controlling and eradicating the population of acarids, and especially aphids, the compounds of the present invention are incorporated as active ingredients into conventional ready-to-use pesticidal compositions, that is, compositions consisting essentially of a solid or liquid inert carrier and an effective amount of the active ingredient, such as solutions, emulsions, sprays, suspensions, dusting powders, granulates or the like, or into concentrate compositions which are diluted with water prior to use, such an emulsion concentrates or wettable powers. The effective acaricidal concentration of the active ingredient according to the present invention is the ready-to-use compositions and the diluted concentrates isbetween about 50 and 2000 ppm, preferably 100 to 1000 ppm. The concentrate compositions may contain from about 5 to 95% by weight of active ingredient.

On an amount per unit area basis, the compounds are applied at the rate of 0.2 to 10 kg/hectare, preferably 0.5 to 3 kg/hectare, depending upon the severity of infestation.

The following is an illustrative example of acaricidal concentrate composition containing a compound of the present invention as an active ingredient. The parts are parts by weight.

EXAMPLE 15

Wettable powder

| | |
|---|---|
| Cyclopropyl-imino-O-n-hexadecyl ester nitrate | 20 parts |
| Merpoxen NO 90 (emulsifier) | 10 " |
| Colloidal silicic acid (carrier) | 10 " |
| Chinafill | 60 " |

The inredients are admixed with each other, and the mixture is milled into a homogeneous powder, which is then diluted with water to form a sprayable aqueous suspension.

Any one of the other compounds embraced by formula I, or an acid addition salt thereof, may be substituted for the particular active ingredient in Example 15.

Likewise, the amount of active ingredient in this illustrative example may be varied, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

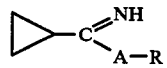

wherein

A is oxygen or —NH—, and

R is alkyl of 3 to 22 carbon atoms when A is oxygen, or alkyl of 2 to 22 carbon atoms when A is —NH—, or alkenyl of 3 to 18 carbon atoms, or an acid addition salt thereof.

2. A compound of claim 1, where A is oxygen and R is oleyl.

3. A compound of claim 1, where A is oxygen and R is n-butyl.

4. A compound of claim 1, where A is oxygen and R is hexadecyl.

* * * * *